United States Patent [19]

Su et al.

[11] Patent Number: 4,968,675
[45] Date of Patent: Nov. 6, 1990

[54] NON-HEMOLYTIC LAZAROID PARENTERAL FORMULATION

[75] Inventors: Ching-Chiang Su, Portage; Teresa Harshman, Richland, both of Mich.

[73] Assignee: Upjohn, Kalamazoo, Mich.

[21] Appl. No.: 264,471

[22] Filed: Oct. 28, 1988

[51] Int. Cl.$^5$ .............................................. A61K 31/58
[52] U.S. Cl. ..................................... 514/176; 514/922
[58] Field of Search ................................ 514/176, 922

[56] References Cited

U.S. PATENT DOCUMENTS

| | | | |
|---|---|---|---|
| 4,497,805 | 2/1985 | Phillipps et al. | 260/397.1 |
| 4,515,786 | 5/1985 | Phillipps et al. | 260/397.45 |
| 4,664,916 | 5/1987 | Fukuda | 424/195.1 |

FOREIGN PATENT DOCUMENTS

WO87/01706  3/1987  World Int. Prop. O. .

OTHER PUBLICATIONS

Cancer Chemotherapy Reports, Part I, 58, 171 (1974).
J. Pharm. Exptl. Ther., 196, 525 (1976).

Primary Examiner—Joseph A. Lipovsky

[57] ABSTRACT

16α-Methyl-21-[4-[2,6-bis(1-pyrrolidinyl)-4-pyrimidinyl]-1-piperazinyl]pregna-1,4,9(11)-triene-3,20-dione monomethanesulfonate causes hemolysis when injected. However, when formulated with a citric acid/sodium citrate both the hemolysis and hypotension side effects are prevented.

2 Claims, No Drawings

NON-HEMOLYTIC LAZAROID PARENTERAL FORMULATION

BACKGROUND OF THE INVENTION

1. Field of the Invention

The present invention involves a pharmaceutical formulation which permits injection of an amino-steroid drug without hemolysis.

2. Description of the Related Art

16α-Methyl-21-[4-[2,6-bis(1-pyrrolidinyl)-4-pyrimidinyl]-1-piperazinyl]pregna-1,4,9(11)-triene-3,20-dione is known as the free base, the monomethanesulfonate, dimethanesulfonate or hydrochloride salts, see International Publication No. W087/01706.

Cancer Chemotherapy Reports Part I, 58, 171 (1974) and J. Pharm. Exptl. Ther., 196, 525 (1976) report that ellipticine (an antineoplastic agent active against L1210 lymphocytic leukemia) causes hemolysis and hypotension in dogs and monkeys following intravenous injection. The hemolysis was prevented when ellipticine was prepared in 300 milliosmoles citrate buffer, pH=4.0. Even though hemolysis was prevented, ellipticine still produced hypotension, bradycardia and an increase in carotid artery blood flow.

The pharmaceutical formulation of the present invention not only prevents hemolysis but it also prevents hypotension.

A presentation of the composition of the present invention was made on Dec. 7, 1987 at Poster Session N-4 (N 07-W-02) of the Pharmaceutics and Pharmaceutical Technology section of the Japanese-United States Congress of Pharmaceutical Sciences' meeting.

SUMMARY OF INVENTION

Disclosed is a parenteral pharmaceutical composition comprising:

16α-Methyl-21-[4-[2,6-bis(1-pyrrolidinyl)-4-pyrimidinyl]-1-piperazinyl]pregna-1,4,9(11)-triene-3,20-dione monomethanesulfonate, dimethanesulfonate or hydrochloride: 0.5–5.0 mg/ml
Citric Acid Hydrate: 2–40 mM
Sodium Citrate Dihydrate: 0.05–6.4 mM
Sodium Chloride: 3–5 mg/ml
pH: 3.0
Osmolality: 180–185 mOsm/kg
Water for injection USP, qsad

DETAILED DESCRIPTION OF THE INVENTION

The pharmaceutically active agent, 16α-methyl-21-[4-[2,6-bis(1-pyrrolidinyl)-4-pyrimidinyl]-1-piperazinyl]pregna-1,4,9(11)-triene-3,20-dione (LAZAROID), is known, see W087/01706 and J. Neurosurgery 68, 456 (1988). It is useful in emergency situations in treating head injury and stroke. Because it is useful in emergency situations, the preferred route of administration is intravenous.

When the LAZAROID was injected intravenously in cats, dogs and monkeys, the drug was found to produce hemolysis. When the LAZAROID was compounded in a parenteral formulation of 50 mM citric acid/10 mM sodium citrate, hemolysis was eliminated but hypotension was measured in cats. However, when compounded in a parenteral formulation of suitable concentrations of sodium citrate/citric acid appropriately adjusted for pH and osmolality (with sodium chloride) neither hemolysis nor hypotension occurred.

It is preferred that the LAZAROID be used as the monomethanesulfonate, bismethanesulfonate or hydrochloride; it is more preferred the LAZAROID be used as the monomethanesulfonate. It is preferred that the amount of the LAZAROID be from about 0.5 mg/ml to about 5.0 mg/ml; more preferably about 1.5 mg/ml. It is preferred that the amount of citric acid used be from about 2 to about 40 mM; more preferably about 20 mM. It is preferred that the sodium citrate be the dihydrate and that the amount be from about 0.05 to about 6.4 mM; more preferably about 3 to about 3.5 mM; most preferably 3.2 mM. It is preferred that the pH be 3.0. It is preferred that sufficient sodium chloride be used to obtain an osmolality of about 180–185 mOsm/kg; more preferably that 4.5 mg/ml of sodium chloride be used to obtain an osmolality of 183 mOsm/kg.

The parenteral pharmaceutical composition is formulated by first putting the water for injection into two vessels, the No 1 with about 90–95% and No 2 with about 5–10%. The citric acid is dissolved in the water in vessel No 1. About 7% of the citric acid stock solution is transferred to vessel No 3. The LAZAROID is dissolved in vessel No 1. The sodium citrate and sodium chloride are dissolved in vessel No 3. Slowly with stirring the contents of vessel No 3 are added to vessel No 1. Some of the contents of vessel No 2 are used to rinse vessel No 3 and the contents added to vessel No 1. The water from vessel No 2 are used to bring vessel No 1 to final correct volume. The mixture is sterilized, preferably by filtration.

The parenteral pharmaceutical composition of the invention is given IV. Further, it can be given as a one time shot or a continuous IV infusion.

The pharmaceutical composition of this invention is to be used according to the teaching of W087/01706, preferably at a daily dose of <20 mg/kg, more preferably at a daily dose of about 6 mg/kg.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

Non-hemolytic Parenteral Formulation of 16α-methyl-21-[4-[2,6-bis(1-pyrrolidinyl)-4-pyrimidinyl]-1-piperazinyl]pregna-1,4,9(11)-triene-3,20-dione monomethanesulfonate

| Item | Amount |
| --- | --- |
| 16α-Methyl-21-[4-[2,6-bis(1-pyrrolidinyl)-4-pyrimidinyl]-1-piperazinyl]pregna-1,4,9(11)-triene-3,20-dione monomethanesulfonate | 1.5 mg/ml |
| Citric Acid Hydrate | 20 mM |
| Sodium Citrate Dihydrate | 3.2 mM |
| Sodium Chloride | 4.5 mg/ml |
| pH adjusted with sodium hydroxide or hydrochloric acid to | 3.0 |

| Item | Amount |
| --- | --- |
| Osmolality | 183 mOsm/kg |
| Water for injection, USP qsad | |

The parenteral pharmaceutical composition is prepared by placing water for injection USP in vessel No 1. Transfer about 5-10% of the water for injection to vessel No 2. Cover securely to prevent reabsorption of atmospheric oxygen and reserve as a rinse and for final volume adjustment.

Completely dissolve citric acid into the water for injection in vessel No 1.

Transfer approximately 7% of the citric acid stock solution to vessel No 3. Sparge with filtered nitrogen. Keep well covered and reserve. Discontinue nitrogen sparging and flush. Turn mixer on low and completely dissolve the drug in the remaining citric acid stock solution in vessel No 1. Keep vessel No 1 well covered. Apply filtered nitrogen flush over the solution after drug is well wetted.

Dissolve the sodium citrate and then the sodium chloride in vessel No 3. Keep vessel No 3 well covered. Slowly add with stirring the sodium citrate/sodium chloride solution to the vessel No 1. Rinse vessel No 2 with approximately 5-10% of the reserved water for injection and transfer the rinse to vessel No 1. Repeat the rinse and transfer step with another 5-10% of water.

Add the reserved water for injection to bring to final volume.

Mix the solution for at least 30 minutes to insure a homogeneous solution. Apply gentle nitrogen sparging and flush to the solution. Keep vessel No 1 well covered.

Sterilize by filtration.

We claim:

1. A parenteral pharmaceutical composition comprising:

16α-Methyl-21-[4-[2,6-bis(1-pyrrolidinyl)-4-pyrimidinyl]-1-piperazinyl]pregna-1,4,9(11)-triene-3,20-dione monomethanesulfonate, dimethanesulfonate or hydrochloride: 0.5-5.0 mg/ml
Citric Acid Hydrate: 2-40 mM
Sodium Citrate Dihydrate: 0.05-6.4 mM
Sodium Chloride: 3-5 mg/ml
pH: 3.0
Osmolality: 180-185 mOsm/kg
Water for injection USP, qsad.

2. A parenteral pharmaceutical composition comprising:

16α-Methyl-21-[4-[2,6-bis(1-pyrrolidinyl)-4-pyrimidinyl]-1-piperazinyl]pregna-1,4,9(11)-triene3,20-dione monomethanesulfonate: 1.5 mg/ml
Citric Acid Hydrate: 20 mM
Sodium Citrate Dihydrate: 3.2 mM
Sodium Chloride: 4.5 mg/ml
pH: 3.0
Osmolality: 183 mOsm/kg

* * * * *

UNITED STATES PATENT AND TRADEMARK OFFICE
CERTIFICATE OF CORRECTION

PATENT NO. : 4,968,675

DATED : Nov. 6, 1990

INVENTOR(S) : Ching-Chiang Su and Teresa Harshman

It is certified that error appears in the above-identified patent and that said Letters Patent is hereby corrected as shown below:

On the title page, add the following:
 --Attorney, Agent or Firm — Bruce Stein --; and In column 2, line 35, after the word "continuous", omit the period (.).

Signed and Sealed this

Twenty-first Day of April, 1992

Attest:

HARRY F. MANBECK, JR.

*Attesting Officer*      *Commissioner of Patents and Trademarks*